(12) United States Patent
Bellone et al.

(10) Patent No.: US 8,993,232 B2
(45) Date of Patent: Mar. 31, 2015

(54) IDENTIFICATION OF THE CAUSATIVE MUTATION FOR LEOPARD COMPLEX SPOTTING AND CONGENITAL STATIONARY NIGHT BLINDNESS IN EQUINES AND A METHOD FOR TESTING FOR SAME

(75) Inventors: Rebecca Bellone, Valrico, FL (US); Heather Marie Holl, Brooktondale, NY (US); Samantha Ann Brooks, Van Etten, NY (US); George Forsyth, Aberdeen, CA (US)

(73) Assignees: Cornell University, Ithaca, NY (US); University of Saskatchewan, Saskatoon, Saskatchewan, CA (US)

(*) Notice: Subject to any disclaimer, the term of this patent is extended or adjusted under 35 U.S.C. 154(b) by 573 days.

(21) Appl. No.: 13/373,911

(22) Filed: Dec. 5, 2011

(65) Prior Publication Data

US 2012/0145092 A1    Jun. 14, 2012

Related U.S. Application Data

(60) Provisional application No. 61/419,540, filed on Dec. 3, 2010.

(51) Int. Cl.
*C07H 21/04* (2006.01)
*C12Q 1/68* (2006.01)

(52) U.S. Cl.
CPC ............ *C12Q 1/6883* (2013.01); *A01K 2227/10* (2013.01); *C12Q 2600/124* (2013.01); *C12Q 2600/156* (2013.01)
USPC .......... 435/6.1; 435/6.12; 435/91.1; 435/91.2; 536/23.1; 536/24.3

(58) Field of Classification Search
None
See application file for complete search history.

(56) References Cited

U.S. PATENT DOCUMENTS

| 5,474,796 A | 12/1995 | Brennan |
| 2011/0104687 A1 | 5/2011 | Grahn et al. |

FOREIGN PATENT DOCUMENTS

WO    2009/105890    9/2009

OTHER PUBLICATIONS

Bellone et al. (Briefing in Functional Genomics, vol. 9, No. 3, pp. 193-207, Mar. 29, 2010).*
Bellone II (PLOS One, vol. 8, No. 10, pp. e78280, Oct. 2013).*
Antonellis et al. (Genbank Accession No. AC211096, NISC Comparative Sequencing Initiative, Oct. 2007).*
Nelson, J., et al., "Association of an Insertion in TRPM1 with Leopard Complex (LP) Spotting and Congenital Stationary Night Blindness (CSNB) in Horses", Poster presented by J. Nelson at the Plant and Animal Genome Conference XIX, San Diego, CA, Jan. 2011.
Sandmeyer Lynne S et al: "Clinical and electroretinographic characteristics of congenital stationary night blindness in the Appaloosa and the association with the leopard complex", Veterinary Ophthalmology, 2007, vol. 10, No. 6, pp. 368-375.
Bellone Rebecca R et al: "Differential gene expression of TRPM1, the potential cause of congenital stationary night blindness and coat spotting patterns (LP) in the Appaloosa horse (*Equus caballus*)", Genetics, vol. 179, No. 4, 2008, pp. 1861-1870.
Bellone, R.R., et al., "Fine-mapping and mutation analysis of TRPM1: a candidate gene for leopard complex (LP) spotting and congenital stationary night blindness in horses", Briefings in Functional Genomics, 2010, vol. 9, No. 3, pp. 193-207.
Terry R B et al: "Assignment of the appaloosa coat colour gene (LP) to equine chromosome 1.", Animal Genetics, 2004, vol. 35, No. 2, Apr. 2004, pp. 134-137.
Bellone, R.R., et al., "Association analysis of candidate SNPs in TRPM1 with leopard complex spotting (LP) and congenital stationary night blindness (CSNB) in horses", Animal Genetics, 2010, vol. 41, Suppl. 2, p. 207.
Sandmeyer, L.S., et al., "Congenital stationary night blindness is associated with the leopard complex in the miniature horse", Veterinary Ophthalmologists, 2011, pp. 1-5.
Wang Huai-Peng et al: "Distribution profiles of transient receptor potential melastatin-related and vanilloid-related channels in prostatic tissue in rat", Asian Journal of Andrology, 2007, vol. 9, No. 5, pp. 634-640.
Zhiqi Song et al: "Human melastatin 1 (TRPM1) is regulated by MITF and produces multiple polypeptide isoforms in melanocytes and melanoma", Melanoma Research, Lippincott Williams & Wilkins, 2004, vol. 14, No. 6, pp. 509-516.
Sandmeyer Lynne S et al: "Diagnostic ophthalmology. Congenital stationary night blindness (CSNB).", The Canadian Veterinary Journal, 2006, vol. 47, No. 11.
Bellone, R. et al.: 'Comparative mapping of oculocutaneous albinism type II (OCA2), transient receptor potential cation channel, subfamily M member 1 (TRPM1) and two equine microsatellites, ASB08 and 1CA43, among four equid species by fluorescence in situ hybridization.' Cytogenet. Genome Res. vol. 114, No. 1, 2006, p. 93A.
Xiao X.S. et al.: 'CSNB1 in Chinese families associated with novel mutations in NYX.' J. Hum. Genet. vol. 51, No. 7, 2006, pp. 634-640.
Zeitz, C. et al.: 'Mutations in CABP4, the gene encoding the Ca2+-binding protein 4, cause autosomal recessive night blindness.' Am. J. Hum. Genet., 2006, vol. 79, No. 4, pp. 657-667.
Bellone, R. et al.: 'Analysis of a SNP in exon 7 of equine OCA2 and its exclusion as a cause for appaloosa spotting.' Animal. Genetics., 2006, vol. 37, No. 5, p. 525.

(Continued)

*Primary Examiner* — Jeanine A Goldberg
(74) *Attorney, Agent, or Firm* — Robert C. Netter, Jr.; Kathleen D. Rigaut; Dann, Dorfman, Herrell & Skillman

(57) ABSTRACT

Methods are provided for determining whether or not a horse is genetically normal, is a carrier of, or is affected with or predisposed to Congenital Stationary Night Blindness and/or leopard complex spotting. The method is based on detection of an insertion in an intron in the horse Transient Receptor Potential Cation Channel, Subfamily M, Member 1 (TRPM1) gene.

9 Claims, 7 Drawing Sheets

(56) References Cited

OTHER PUBLICATIONS

Predicted: *Equus caballus* similar to transient receptor potential cation channel, subfamily M, member 1 (TRPM1), mRNA', Database Genbank [Online] Jun. 25, 2007, XP003027621 Database accession No. XM 001492235.

Bellone, R.: 'Sighting the Genetic Cause of Leopard Complex Spotting and Congenital Stationary Night Blindness in Horses as a practical application of horse genomics for ophthalmologists.' Dorothy Havemeyer Foundation Equine Ophthalmology Workshop, West Palm Beach, Florida, Apr. 2011.

Roll, H.M. et al.: 'Next-Generation Transcriptome Sequencing in the Horse: Deciphering the Genetic Cause of Leopard Complex Spotting (LP) and Congenital Stationary Night Blindness.' Poster presented by H. Holl at the Plant and Animal Genome Conference XIX, San Diego, CA, Jan. 2011.

Bellone, R.R. et al.: 'An Insertion in TRPM1, the Genetic Cause of Leopard Complex (LP) Spotting and Congenital Stationary Night Blindness (CSNB) in Horses.' Presented as an oral presentation by R. Bellone during the Equine workshop at the Plant and Animal Genome Conference XIX, San Diego, CA, Jan. 2011.

* cited by examiner

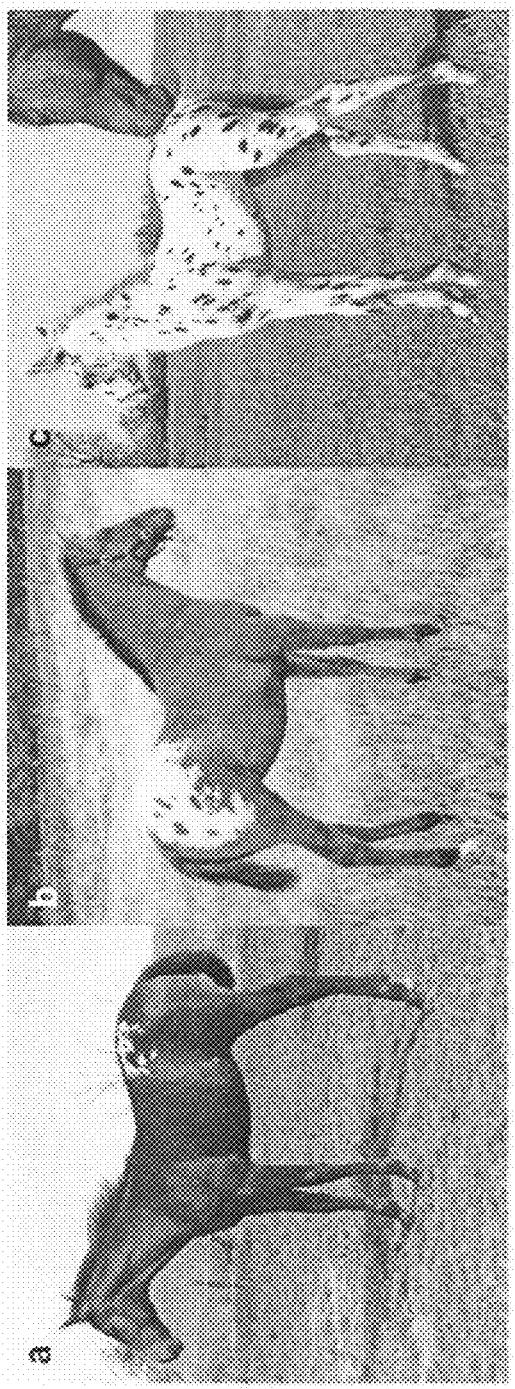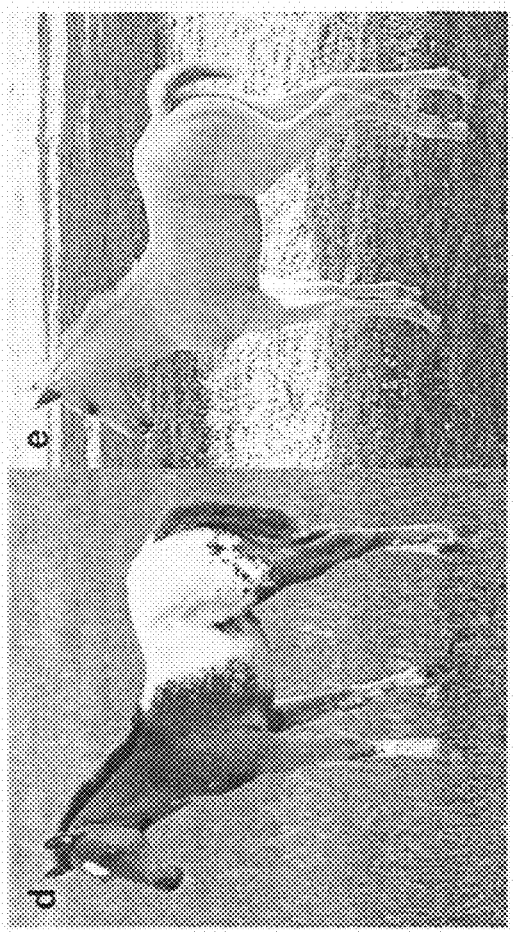
Figure 1

CTGGGGTGCCGGGGTCCCGCCCCGGCGGAGTCCAGGTTCCTGAGGGATGGA
CGGCGTCGGCGCGATGAGGGAGGGGAAAATAAAGGGGACGTGAGACTTGGGT
TGGTGTTAGCAAGTCCGACTTTACTGTGCACAAGTGTCGTTTATATATTTTTCAG
GATTAGTACAGAAATAGTTTTACAAATATTCTCAGAGAGATAAGGAAGTAAGAAA
CGAGCACAAGAATATTTATTAGCATTCCATTCTATAGAGCATAAGGTTAATGATC
GTCTTCTCTGCAATTAACTAGTGTTTGTTGTCTCTAAGCTAAAGGAGATAGGTAC
CTAGGCGTCTGTTGTAATTCATGGTAAAGTTAAATCAAAGAGAGAAGGTCCAGG
CCTCCGGACAGGACAGCAGTCTGTCTGGTTACATCCTGGTGGAGCCATCCCTG
CCTCCCTCAATCATTTACGTCATTAGTGTAGATGGTTAATGGGAACAAAAGGCG
ACTCCAGGGTGTCTTATCCCCAGGGCTATCTGCATTCTCAGCGGGCAGTTAAAC
ATCTTTACTTTTCGCGCCCTTTAGGGGGTGGAAGCATTCCTTTGTCTTTTAGAT
TGTAGAGCTAACGGTCCCTTAAGTACACTGCCGGAGAAAGTATCATATTGTTAG
TGAAGTAAAGGGCTGAAAAGCTAAGCTAAACTATAAATCTTCAAGAATAAAAAG
AGAAATAAGTACACACATAACCTTGATAGAAAGCATGCATATAATTCAGAAAATA
TCGGGGGTGTTGGCCGGCCATTCTTCACCGAGGGGCATTCTTGCACCCCTCGG
CCCTTCTACTCACCAATTATTTATTGTTTATTGCTTTTAGGAGAAAACCTCTATAA
CATTTTAACAGAAAGCAGAAGGTCAAGAATAATATATAGATACTTCTTGATCATC
CAATTAACCAGCAAACTTAGAAGGACGATGCATATGTATATTTAGACAAAGAACT
GGAGGGAGAAGGAAACATTAACCAGATGGAGGCCATAAACCTAATTCGACATC
TTATCTGGGCAGGATTCCTTTCTGATTGTCTCACATGGGACTGTGTGCTCCTCC
ATTAATTAACTGAAAATATCTTGAAAGTTACCTGCAGGTGGTCACATTCTCTTA
CTGTATCTAATTTTCCCGGGAGGTAGTGCCTCCCAAGCAGCCACCCAAAGGAG
TGAAAACTGGAGGTTAAGAAAGGAAAAGGAATGAAGGGCAGTTAAAAGCAGCA
CAGGTTTCAGAACTATGTGAGGGGCTGGCCGGTTATTCTTCACCAAGGGGCGA
CCCTGCACCCCTCAGCGTTAATCGGCTGGACCCTGTCAAACAGCCGATCAAAT
GATGTAGCCACGGCTCCCAGCACTGGGG (SEQ ID NO:1)

Figure 4

SEQUENCE LISTING

<160> NUMBER OF SEQ ID NOS: 4

<210> SEQ ID NO 1
<211> LENGTH: 1378
<212> TYPE: DNA
<213> ORGANISM: Equus caballus

<400> SEQUENCE: 1

```
ctggggtgcc ggggtcccgc cccggcggag tccaggttcc tgagggatgg acggcgtcgg      60
cgcgatgagg gaggggaaaa taaggggac gtgagacttg ggttggtgtt agcaagtccg     120
actttactgt gcacaagtgt cgtttatata tttttcagga ttagtacaga aatagtttta     180
caaatattct cagagagata aggaagtaag aaacgagcac aagaatattt attagcattc     240
cattctatag agcataaggt taatgatcgt cttctctgca attaactagt gtttgttgtc     300
tctaagctaa aggagatagg tacctaggcg tctgttgtaa ttcatggtaa agttaaatca     360
aagagagaag gtccaggcct ccggacagga cagcagtctg tctggttaca tcctggtgga     420
gccatccctg cctccctcaa tcatttacgt cattagtgta gatggttaat gggaacaaaa     480
ggcgactcca gggtgtctta tccccagggc tatctgcatt ctcagcgggc agttaaacat     540
ctttactttt tcgcgccctt taggggtgg aagcattcct ttgtcttta gattgtagag     600
ctaacggtcc cttaagtaca ctgccggaga aagtatcata ttgttagtga agtaaagggc     660
tgaaaagcta agctaaacta taaatcttca agaataaaaa agagaaataa gtacacacat     720
aaccttgata gaaagcatgc atataattca gaaaatatcg ggggtgttgg ccggccattc     780
ttcaccgagg ggcattcttg caccccctcgg cccttctact caccaattat ttattgttta     840
ttgcttttag gagaaaacct ctataacatt ttaacagaaa gcagaaggtc aagaataata     900
tatagatact tcttgatcat ccaattaacc agcaaactta gaaggacgat gcatatgtat     960
atttagacaa agaactggag ggagaaggaa acattaacca gatggaggcc ataaacctaa    1020
ttcgacatct tatctgggca ggattccttt ctgattgtct cacatgggac tgtgtgctcc    1080
tccattaatt aactgaaaaa tatcttgaaa gttacctgca ggtggtcaca ttctcttact    1140
gtatctaatt ttcccgggag gtagtgcctc ccaagcagcc acccaaagga gtgaaaactg    1200
gaggttaaga aaggaaaagg aatgaagggc agttaaaagc agcacaggtt tcagaactat    1260
gtgaggggct ggccggttat tcttcaccaa ggggcgaccc tgcaccctc agcgttaatc    1320
ggctggaccc tgtcaaacag ccgatcaaat gatgtagcca cggctcccag cactgggg     1378
```

<210> SEQ ID NO 2
<211> LENGTH: 20
<212> TYPE: DNA
<213> ORGANISM: Equus caballus

<400> SEQUENCE: 2

```
ccgacttggg tagcaactga                                                   20
```

```
<210> SEQ ID NO 3
<211> LENGTH: 20
<212> TYPE: DNA
<213> ORGANISM: Equus caballus

<400> SEQUENCE: 3
ctcggcaatc agtgaatgaa                                              20

<210> SEQ ID NO 4
<211> LENGTH: 20
<212> TYPE: DNA
<213> ORGANISM: Equus caballus

<400> SEQUENCE: 4
aagggcagtt aaaagcagca                                              20
```

IDENTIFICATION OF THE CAUSATIVE MUTATION FOR LEOPARD COMPLEX SPOTTING AND CONGENITAL STATIONARY NIGHT BLINDNESS IN EQUINES AND A METHOD FOR TESTING FOR SAME

RELATED APPLICATIONS

This application claims the benefit under 35 USC §119(e) of U.S. provisional application No. 61/419,540 filed on Dec. 3, 2010, which is incorporated herein by reference in its entirety.

INCORPORATION OF SEQUENCE LISTING

A computer readable form of the Sequence Listing "13764-154_SequenceListing.txt" (8,192 bytes), submitted via EFS-WEB and created on Dec. 5, 2011, is herein incorporated by reference.

FIELD

The present disclosure relates generally to inherited diseases and coat patterns observed in equines. More particularly, the present disclosure relates to detecting the causative mutation for leopard complex spotting and congenital stationary night blindness in equines.

BACKGROUND

Horses (*Equus Caballus*) are among the domesticated animals valued by breeders and enthusiasts for their variety and beauty of coat color and patterns. The genetic mechanisms involved in several different variations of coloration and patterning in horses have been reported including; chestnut, frame overo, cream, black, silver dapple, sabino-1 spotting, tobiano spotting and dominant white spotting (Marklund et al. 1996; Metallinos et al. 1998; Mariat et al. 2003; Reider et al. 2003; Brunberg et al. 2006; Brooks and Bailey 2005; Brooks et al., 2007; Haase et al. 2007). Although there are several inherited ocular diseases reported in the horse (cataracts, glaucoma, anterior segment dysgenesis, and congenital stationary night blindness), the causative genetic mutations and the pathogenesis of some of these ocular disorders remain unknown.

Appaloosa spotting is characterized by patches of white in the coat that tend to be symmetrical and centered over the hips. In addition to the patterning in the coat, appaloosa spotted horses have three additional pigmentation traits; striped hooves, readily visible nonpigmented sclera around the eye, and mottled pigmentation around the anus, genitalia, and muzzle (Sponenberg and Beaver 1983). The extent of spotting varies widely among individuals, resulting in a collection of patterns which are termed the "leopard complex" (Sponenberg et al. 1990). This variation encompasses a broad spectrum of patterns; including those possessing very minimal patches on the rump (known as a "lace blanket"), a white body with many oval or round pigmented spots dispersed throughout (known as "leopard", from which the genetic locus is named), as well as a nearly complete depigmentation (known as "fewspot") (FIG. 1). A single autosomal dominant gene, Leopard Complex (LP), is thought to be responsible for the inheritance of these patterns and associated traits, while modifier genes are thought to play a role in determining the amount of white patterning that is inherited (Miller 1965; Sponenberg et al. 1990; Sponenberg et al. 2009). Horses that are homozygous for appaloosa spotting (LP/LP) tend to have fewer spots of pigment in the white patterned areas; these horses are known as "fewspots" (largely white body with little to no spots) and "snowcaps" (white over the croup and hips with little to no spots) (Sponenberg et al. 1990; Lapp & Carr 1998). Leopard complex spotting is characterized as a group of white spotting patterns that occurs in several breeds of horses including, among others, Appaloosas, Knabstruppers, Norikers, Australian spotted ponies, British spotted ponies, Pony of the Americas, and American Miniature horses.

The spotting pattern (aka appaloosa), caused by an incompletely dominant gene (LP), is a highly valued trait in the horse. However, it's highly variable nature and complex inheritance make it difficult for breeders to select homozygous animals for breeding stock in order to increase their production of desirable patterns.

A whole genome scanning panel of microsatellite markers was used to map LP to a 6 cM region on ECA1 (Terry et al. 2004). Prior to the sequencing of the equine genome, two candidate genes Transient Receptor Potential Cation Channel, Subfamily M, Member 1 (TRPM1) and Oculoctaneous Albinism Type II (OCA2) were suggested based on comparative phenotypes in humans and mice (Terry et al. 2004). Both TRPM1 and OCA2 were FISH mapped to ECA1, to the same interval as LP (Bellone et al. 2006a). One SNP in the equine OCA2 gene has been ruled out as the cause for appaloosa spotting (Bellone et al. 2006b).

TRPM1, also known as Melastatin 1 (MLSN1), is a member of the transient receptor potential (TRP) channel family. Channels in the TRP family may permit $Ca^{2+}$ entry into hyperpolarized cells, producing intracellular responses linked to the phosphatidylinositol and protein kinase C signal transduction pathways (Clapham et al. 2001). TRPs are important in cellular and somatosensory perception (Nilius, 2007). Defects in a light-gated TRP channel results in a loss of phototransduction in *Drosophila* (reviewed in Kim, 2004). Although the specific function of TRPM1 in melanogenesis has yet to be described, cellular sensation and intercellular signaling is vital for normal melanocyte migration (reviewed in Steingrimsson et al. 2006). In mice and humans, the promoter region of this gene contains four consensus binding sites for a melanocyte transcription factor, MITF (Hunter et al. 1998; Zhiqi et al. 2004). One of these sites, termed an M-box, is unique to melanocytic expression (Hunter et al. 1998). TRPM1 is downregulated in highly metastatic melanoma cells, suggesting that this protein plays an important role in normal melanogenesis (Duncan et al. 1998).

In humans TRPM1 is expressed in several isoforms (Xu et al. 2001; Fang and Setaluri 2000). The long isoform, termed MLSN-L, is thought to be responsible for $Ca^{2+}$ influx (Xu et al. 2001). It is possible the large relative expression difference that was detected for the long isoform of TRPM1 may interfere with $Ca^{2+}$ signaling in the melanocytes and thus participate in the biological mechanisms of appaloosa spotting (Bellone et al., 2008).

The specific function of TRPM1 in melanocytes is unknown. It has been described as a tumor suppressor that may regulate the metastatic potential of melanomas, as its expression declines with increased metastatic potential (Duncan et al. 1998; Deeds et al. 2000; Duncan et al. 2001). Treatment of pigmented melanoma cells with a differentiation inducing agent upregulated the long isoform of this gene (Fang and Setaluri, 2000). TRPM1 therefore has potential roles in $Ca^{2+}$-dependent signaling related to melanocyte proliferation, differentiation, and/or survival.

One potential role of TRPM1 in melanocyte survival is in interaction with the signaling pathway of the cell surface tyrosine kinase receptor, KIT, and its ligand KITLG. Signaling through the KIT receptor is critical for the growth, survival and migration of melanocyte precursors (reviewed by Erikson, 1993). It has been shown that both phospholipase C activation and $Ca^{2+}$ influx are important in supporting KIT-positive cells (Berger 2006). Stimulation with KIT ligand while blocking $Ca^{2+}$ influx led to a novel form of cell death that is termed activation enhanced cell death (AECD) (Gommerman and Berger 1998). It is possible that during melanocyte proliferation and differentiation, when KIT positive cells are being stimulated by the ligand in vivo, the absence of TRPM1 expression may result in decreased $Ca^{2+}$ influx and ultimately result in AECD. Early melanocyte death could explain LP hypopigmentation patterns.

An association of homozygosity for LP and congenital stationary night blindness (CSNB) has been documented (Sandmeyer et al. 2007 and Sandmeyer et al., 2011). CSNB is characterized by a congenital and non-progressive scotopic visual deficit (Witzel et al. 1977, 1978; Rebhun et al. 1984). Affected horses may exhibit apprehension in dimly lit conditions and may be difficult to train and handle in phototopic (light) and scotopic (dark) conditions (Witzel et al. 1977, 1978; Rebhun et al. 1984). Affected animals occasionally manifest a bilateral dorsomedial strabismus (improper eye alignment) and nystagmus (involuntary eye movement) (Rebhun et al. 1984; Sandmeyer et al. 2007). CSNB is diagnosed by an absent b-wave and a depolarizing a-wave in scotopic (dark-adapted) electroretinography (ERG) (FIG. 2). This ERG pattern is known as a "negative ERG" (Witzel et al. 1977). No morphological or ultrastructural abnormalities have been detected in the retinas of horses with CSNB (Witzel et al. 1977; Sandmeyer et al. 2007). A similar "negative ERG" is seen in the Schubert-Bornshein type of human CSNB (Schubert and Bornshein 1952; Witzel et al. 1978). This type of CSNB is thought to be caused by a defective neural transmission within the retinal rod pathway (Witzel et al. 1977, 1978; Sandmeyer et al. 2007). Rod photoreceptors are most sensitive under scotopic conditions. In the dark, these cells exist in a depolarized state. They hyperpolarize in response to light, and signaling occurs through reductions in glutamate release (Stryer 1991). This hyperpolarization is responsible for the a-wave of the electroretinogram. Normally this results in stimulation of a population of bipolar cells, the ON bipolar cells. The glutamate receptor of the ON bipolar cells is a metabotropic glutamate receptor (MGluR6) and this receptor is expressed only in the retinal bipolar cell layer (Nomura et al. 1994; Nakanishi et al. 1998). The MGluR6 receptors sense the reduction in synaptic glutamate and produce a response that depolarizes the ON bipolar cell (Nakanishi et al. 1998). This depolarization is responsible for the b-wave of the electroretinogram. The ERG characteristics of the Schubert-Bornshein type of CSNB are consistent with a failure in depolarization of the ON bipolar cell (Sandmeyer et al. 2007).

Although the exterior of the eye appears normal in CSNB affected horses, these individuals are blind in low light. Despite the use and breeding of horses with leopard complex spotting for hundreds of years, the association of homozygosity with CSNB was not made until recently due to the difficulty in obtaining a definitive diagnosis, which requires an electroretinagram administered by a Veterinary Ophthalmologist. Although CSNB may not affect the function of an affected horse as a show animal the condition does make necessary careful management to avoid injury, both to the horse and to any handler working with an affected horse in dim light. Breeders and clinicians need to be able to test for LP in order to increase the production of desirable spotting patterns and to more easily and effectively diagnose CSNB.

Decreased expression of TRPM1 has been implicated as the cause for both LP and CSNB (Bellone et al. 2008 and WO/2009/105890). Furthermore, this decreased expression in the horse led others to investigate the role of TRPM1 in ON bipolar cell signalling and in human CSNB. Recently TRPM1 has been shown to be the cation channel closed in response to signalling through MGluR6 and the cause of several forms of human CSNB Bellone et al. 2008; Shen et al. 2009; Morgans et al. 2009; Van Genderen et al. 2009; Audo et al. 2009; Nakamura et al. 2010; Li et al. 2009). LP and CSNB have been fine-mapped in the horse to a 173-kb haplotype on ECA1 and Illumina sequencing identified SNPs in the horse for further investigation (Bellone et al. 2010; WO/2009/105890; US patent application Ser. No. 13/292,688).

SUMMARY

The present disclosure provides a method for determining whether a horse is normal (lp/lp), heterozygous for LP and a carrier for CSNB (LP/lp) or is homozygous for LP (LP/LP).

The method comprises the steps of testing a sample from a horse to identify the presence of an insertion in the horse Transient Receptor Potential Cation Channel, Subfamily M, Member 1 (TRPM1) gene after position 108,297,929 on horse chromosome 1 (ECA1).

In one embodiment, a horse is determined as normal when genetically both alleles of TRPM1 do not contain an insertion after position 108,297,929 on horse chromosome 1. In another embodiment, the horse is determined as heterozygous when one of the alleles of the TRPM1 gene has an insertion after position 108,297,929 on horse chromosome 1. In yet another embodiment, the horse is determined as homozygous when both alleles of the TRPM1 gene have an insertion after position 108,297,929 on horse chromosome 1.

Accordingly, the present disclosure provides a method of screening for, diagnosing or detecting congenital stationary night blindness (CSNB) or detecting or selecting different coat patterns, comprising testing a sample from a horse to identify the presence of an insertion in the TRPM1 gene after position 108,297,929 of horse chromosome 1 (ECA1), wherein absence of an allele with the insertion indicates a genetically normal horse or true solid coat colored horse (lp/lp), the presence of an insertion on one allele indicates a spotted horse heterozygous for LP and a carrier for CSNB (LP/lp) and the presence of the insertion on both alleles indicates a spotted horse homozygous for LP and that the horse is affected with or predisposed to CSNB (LP/LP).

In one embodiment, the insertion consists of a 1378 base pair insertion. In another embodiment, the insertion is as shown in SEQ ID NO:1.

The sample may be tested by amplifying a region surrounding and/or including the insertion site and analyzing the region to determine the presence or absence of the insertion. In one embodiment, three primers are used to amplify the region surrounding and/or including the insertion site, wherein a first primer and a second primer (for example, the primers designated as R and F1 in FIG. 5) amplify a region that is indicative of the wild type allele and the first primer and a third primer (for example, the primers designated as R and F2 in FIG. 5) amplify a region that is indicative of the allele with the insertion. In an embodiment, the region amplified from the first primer and the second primer results in a different size product from the region amplified from the first primer and the third primer and analyzing the region to determine the present or absence of the insertion comprises determining the size of the amplified regions. In a particular embodiment, the three primers comprise the sequences as shown in SEQ ID NOs:2-4.

The sample may also be tested by direct sequencing or by use of a first probe that specifically hybridizes to the insertion allele to identify the presence of the insertion. In an embodiment, a second probe that specifically hybridizes to the wild type TRPM1 allele is used to identify the absence of the insertion. In one embodiment, the first probe and the second probe are differentially detected by size of hybridized product or by a distinct label on each probe.

In an embodiment, the horse is an Appaloosa horse, American Miniature Horse, British Spotted Pony, Pony of the Americas, Noriker, or a Knabstrupper horse.

In another embodiment, the methods disclosed herein further comprise managing the CSNB if the horse is homozygous for the insertion.

In yet another embodiment, the methods disclosed herein further comprise selecting a horse that has no allele with the insertion and a horse that has both alleles with the insertion and breeding the horses together to generate a horse with an LP/lp genotype; selecting two horses, each with both alleles with the insertion and breeding the horses together to generate a horse with an LP/LP genotype; selecting two horses, each with no alleles with the insertion and breeding the horses together to generate a horse with an lp/lp genotype; selecting two horses, each with one allele with the insertion and breeding the horses together to generate a horse with an LP/LP, LP/lp or lp/lp genotype; selecting a horse with one allele with the insertion and a horse with both alleles with the insertion and breeding the horses together to generate a horse with an LP/LP or LP/lp genotype; or selecting a horse with one allele having the insertion and a horse with no alleles with the insertion and breeding the horses together to generate a horse with an LP/lp or lp/lp genotype.

In yet another embodiment, the present disclosure provides a method for selecting horses for breeding that avoids CSNB in all foals, comprising testing a sample obtained from a horse to detect the presence or absence of an insertion after position 108,297,929 on chromosome 1 in one or both alleles and breeding horses that are (i) heterozygous with genetically normal horses; or (ii) homozygous with genetically normal horses, to generate foals for Leopard complex spotting, while avoiding CSNB.

Also provided herein is a probe that specifically hybridizes to the insertion sequence as shown in SEQ ID NO:1 or a primer having the nucleotide sequence as shown in SEQ ID NO 4.

In yet another embodiment, there is provided a kit for screening, detecting or diagnosing congenital stationary night blindness (CSNB) or a predisposition to CSNB in a horse or for detecting or screening horse coat patterns comprising the probes or primers disclosed herein.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 1 is a series of photographs of horses displaying different appaloosa coat color patterns: (a) lace blanket (LP/lp); (b) spotted blanket (LP/lp); (c) leopard (LP/lp); (d) snowcap blanket (LP/LP); and (e) fewspot (LP/LP).

FIG. 4 shows the sequence of the 1378 base pair insertion in the 5' to 3' direction (SEQ ID NO:1).

DETAILED DESCRIPTION

Figure 2:
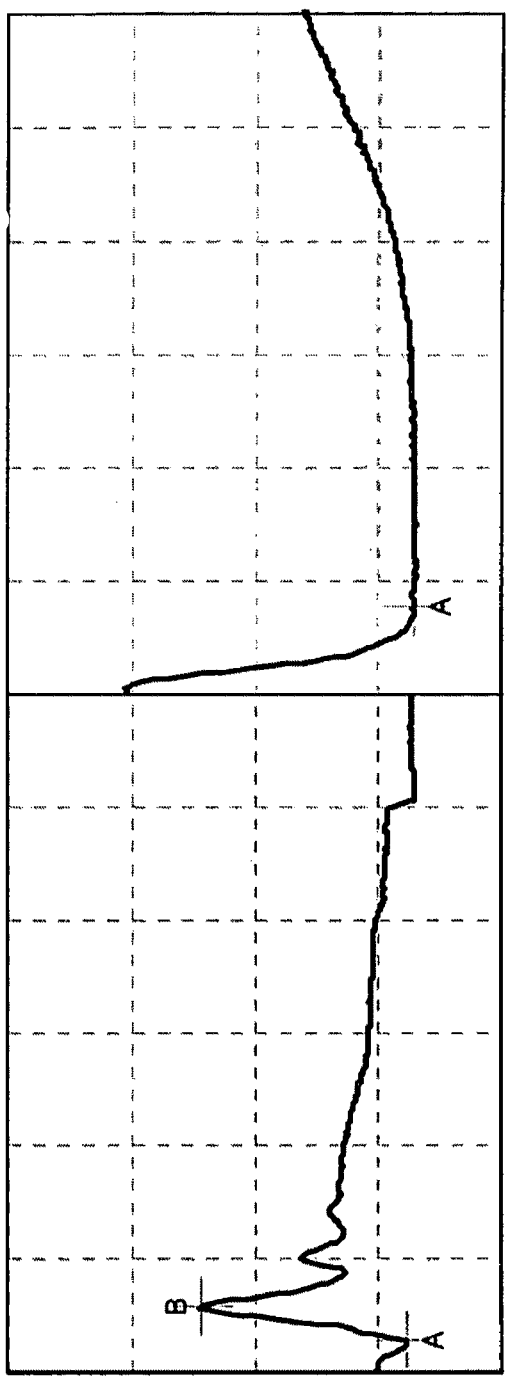
FIG. 2 is a scotopic electroretinogram from an lp/lp Appaloosa (left) and an LP/LP Appaloosa with CSNB (right). Note the absence of a b-wave in the ERG tracing from the LP/LP horse. (50 msec, 100 mV).
Figure 3A:
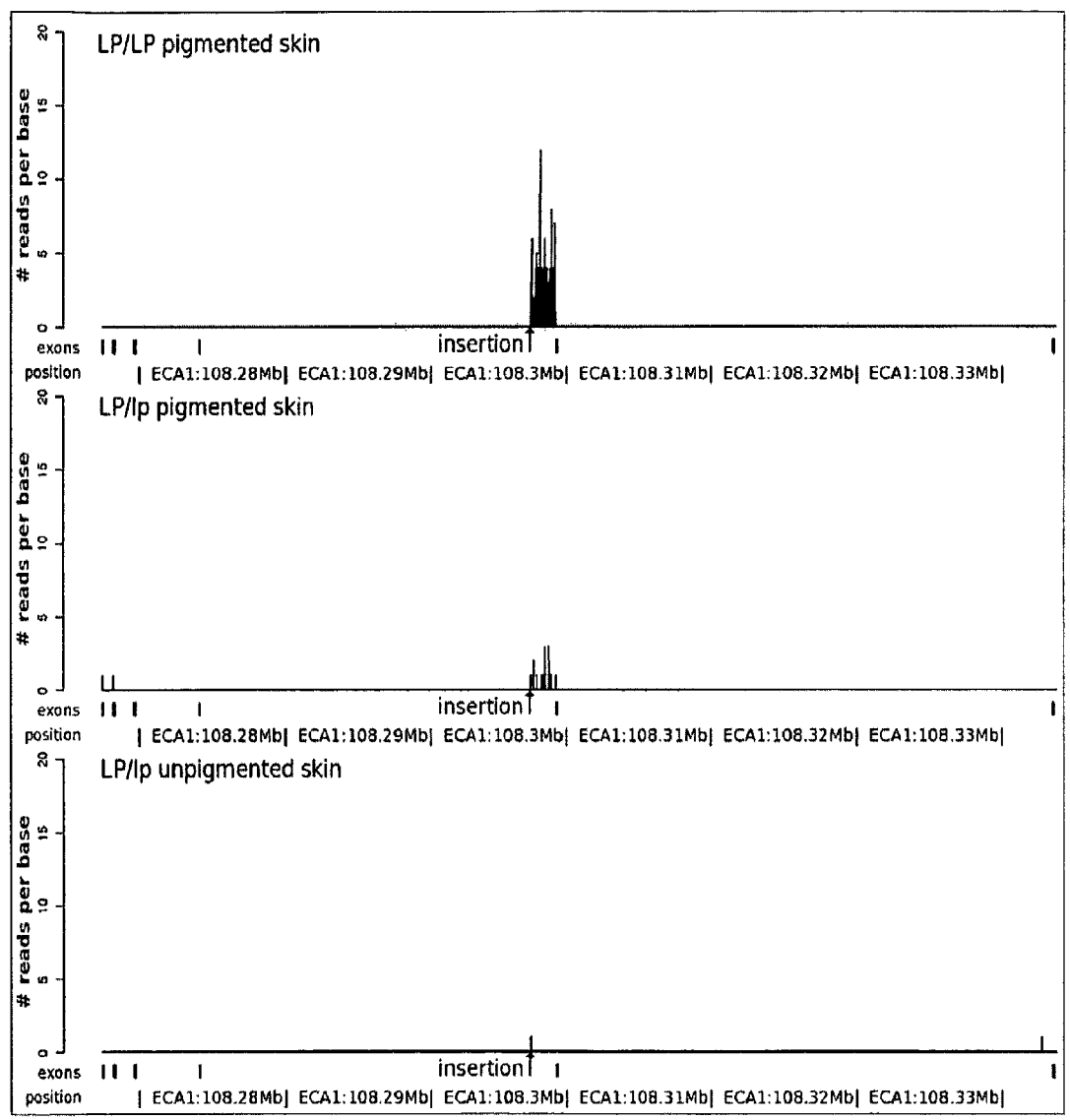
FIG. 3 shows a schematic of the EquCab2 assembly (UCSC Genome Brower) showing the location of the insertion from skin and retina. The insertion was transcribed and detected using RNA-seq technology (Illumina/Solexa, work done at the Cornell CORE). The non-LP horses, did not possess the insertion, and had no sequencing reads aligned to this region.
Figure 3B:
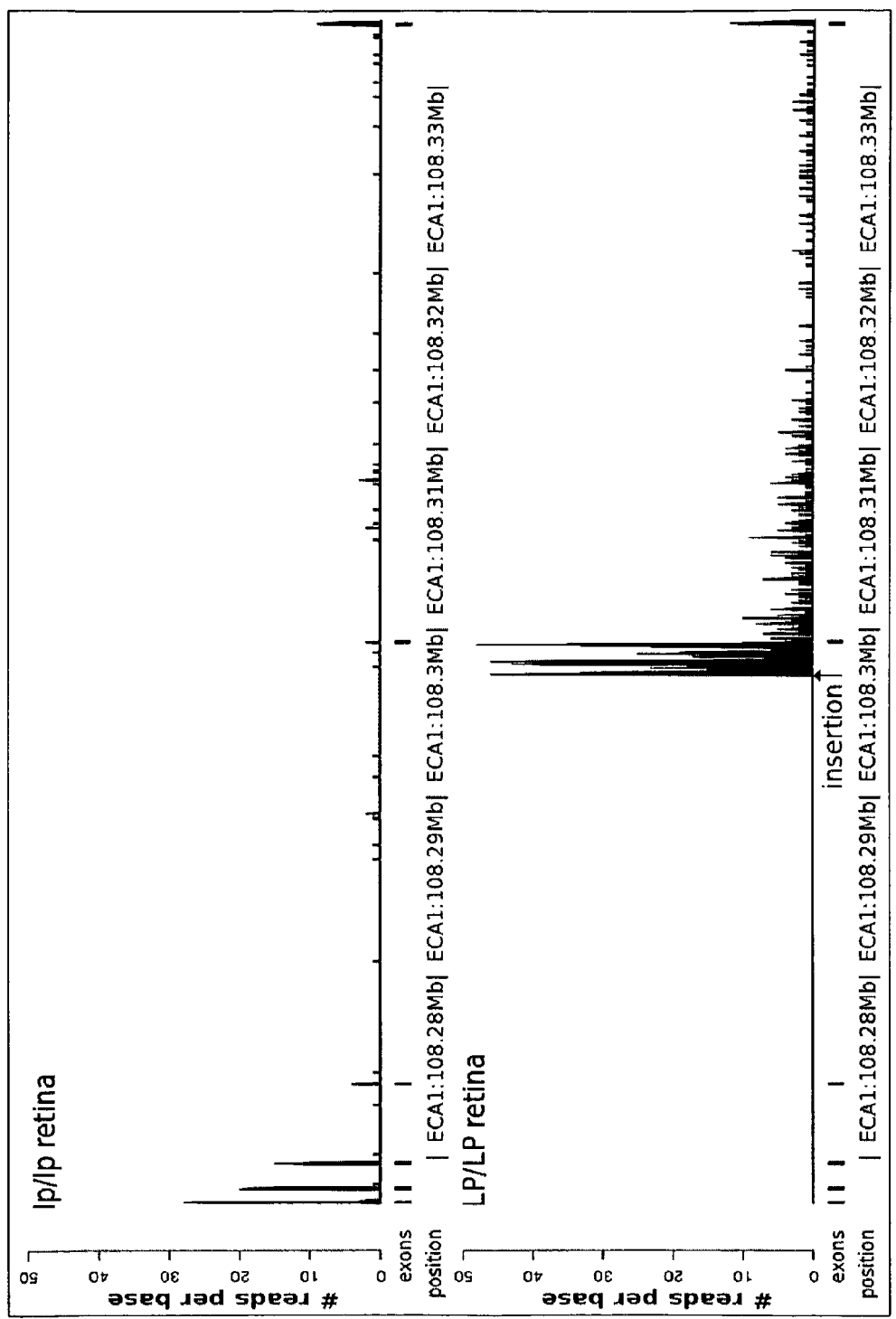
Figure 3C:
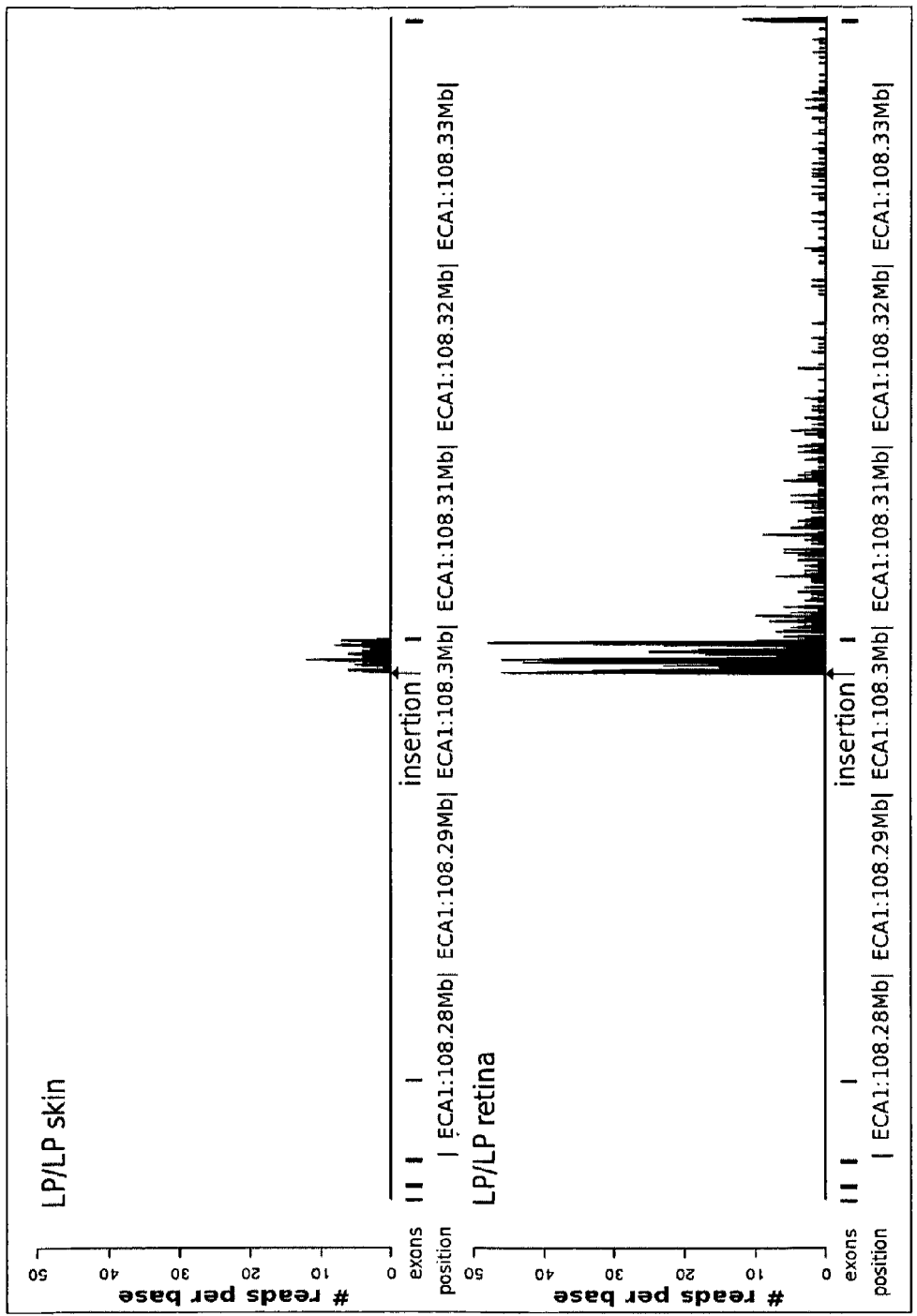

The present inventors have identified an insertion mutation immediately after position 108,297,929 on horse chromosome 1 (ECA1) and have shown this insertion mutation to be the causative mutation of leopard spotting and congenital stationary night blindness.

The term "ECA1" as used herein refers to horse chromosome 1.

The term "horse" as used herein includes all breeds, including, without limitation, Appaloosa, Noriker, Knabstrupper, American Miniature, Pony of the America, Australian spotted pony, British spotted pony, Altai, Mongolian Pony, Colorado Ranger Horse, Falabella, Spanish Mustang, and Karabaier or any other LP carrying breed. In one embodiment, the breed is Appaloosa. In another embodiment, the breed is Knabstrupper. In yet another embodiment, the breed is American Miniature. In a further embodiment, the breed is a British Spotted Pony. In yet a further embodiment, the breed is a Pony of the Americas. In an even further embodiment, the breed is a Noriker.

The term "sample" or "biological sample" as used herein refers to any fluid, cell or tissue sample from a horse, in which DNA or RNA can be isolated. In one embodiment, the sample is a blood sample or serum sample. In another embodiment, the sample is a hair sample. In yet another embodiment, the sample is a skin sample. In yet a further embodiment, the sample is a retinal sample. If the horse has a variation in skin pigmentation, then the skin sample can be pigmented or unpigmented skin. The methods disclosed herein also contemplate prenatal screening, for example, the sample can be from a fetus of a horse. In an embodiment, the presence or absence of the insertion can be determined from DNA or RNA obtained from a horse sample, or from a cDNA amplified from RNA obtained from a horse sample.

The term "TRPM1 gene" refers to the gene encoding the transient receptor potential cation channel, subfamily M member 1 and includes, without limitation, all known TRPM1 genes, including naturally occurring variants, and including those deposited in Genbank with accession number XM_001492235.1 and accession number NM_002420.

The phrase "after position 108,297,929" as used herein refers to the position of the insertion occurring immediately after position 108,297,929 of horse chromosome 1. The insertion occurs after base 108,297,929 and the ends of the insertion have short repeats CTGGG at the beginning and at the end of the insertion. The nucleotides CTGGG are also in the wild type sequence at 108,297,929. Without wishing to be bound by any theory, it is hypothesized that this is how the insertion integrated into this location in the genome.

The phrase "insertion allele" as used herein refers to a form of the TRPM1 gene having an insertion after position 108, 297,929 of horse chromosome 1.

The phrase "wild type allele" as used herein refers to a form of the TRPM1 gene not having an insertion after position 108,297,929 of horse chromosome 1.

Methods to Detect Congenital Stationary Night Blindness:

The present disclosure provides, a method of screening for, diagnosing or detecting congenital stationary night blindness (CSNB) in a horse or for determining whether a horse is a carrier for CSNB comprising testing a sample from a horse to identify the presence of an insertion in one or both alleles of the horse Transient Receptor Potential Cation Channel, Subfamily M, Member 1 (TRPM1) gene after position 108,297, 929 of horse chromosome 1 (ECA1), wherein absence of an allele with the insertion indicates no CSNB, the presence of the insertion on one allele indicates that the horse is a carrier for CSNB and the presence of the insertion on both alleles indicates that the horse is affected with or predisposed to CSNB.

In one embodiment, the insertion is a 1378 base pair insertion. In another embodiment, the insertion is as shown in SEQ ID NO:1.

The term "congenital stationary night blindness" or "CSNB" as used herein refers to a non-progressive, inherited retinal disorder that is characterized by night blindness, decreased visual acuity, myopia, nystagmus and strabismus. It is diagnosed by an absent b-wave and depolarizing a-wave on an electroretinograph (ERG) (see FIG. 2). The term also includes the Schubert-Bornshein type of human congenital stationary night blindness.

The phrase "screening for, diagnosing or detecting congenital stationary night blindness" refers to a method or process of determining if an individual horse has or does not have congenital stationary night blindness, and includes determining the grade or severity of congenital stationary night blindness.

The phrase "determining whether a horse is a carrier for CSNB" refers to a method or process of determining if an individual horse, which does not have congenital stationary night blindness, carries a recessive allele that is causative for congenital stationary night blindness and which may be inherited by the progeny of said horse.

The phrase "testing a sample from a horse to identify the presence of an insertion" as used herein includes, without limitation, obtaining a sample and sequencing a region of DNA or RNA surrounding the insertion site (after position 108,297,929); obtaining a sample and testing the sample for hybridization with a probe that hybridizes to the insertion allele and a probe that hybridizes to the wild type TRPM1 allele and differentially detecting the presence of each probe, or obtaining a sample and amplifying from the sample a region surrounding and/or including the insertion site after position 108,297,929 and analyzing the amplified region for the presence of the insertion, for example, detecting the size of the amplified region or by sequencing the region. The presence of the insertion could also be identified by Restriction Fragment Length Polymorphism, employing restriction sites containing in flanking genomic regions combined with unique restriction sites contained with the insert sequence. In one embodiment, three primers are used wherein a first primer and a second primer that flank the insertion site amplify the region of the wild type allele and the first primer and a third primer that is located within the insertion sequence amplify the region of the allele with the insertion sequence, wherein the amplified regions are differentially detectable (see, for example, FIGS. 5 and 6). Primers and probes useful in the methods disclosed herein are further described below.

The phrase "differentially detectable" as used herein refers to the ability to differentiate between two products (amplified regions or hybridized regions or restriction fragments), for example, based on size or label.

In an embodiment, the method further comprises managing the CSNB in the horse if the horse is homozygous for the insertion. In an embodiment, the method further comprises treating the horse for CSNB if the horse is homozygous for the insertion.

The phrase "managing the CSNB in the horse" as used herein refers to managing strategies to minimize the risk of injury to both the horse and the owner/handler, including without limitation, installing night lighting in a paddock or in shelter and stalls, using proper fencing such as solid or break away materials designed to minimize injuries, and pasturing with non-aggressive companion animals.

Methods to Detect or Select Coat Patterns in Horses

Predicting the genotype of LP from a phenotype can be difficult because of the variability in pattern and complications when other spotting patterns caused by different loci are present. Accordingly, in another aspect, the disclosure provides a method of detecting or selecting different coat patterns in a horse comprising testing a sample from a horse to identify the presence of an insertion in the horse Transient Receptor Potential Cation Channel, Subfamily M, Member 1 (TRPM1) gene after position 108,297,929 on horse chromosome 1 (ECA1) wherein absence of an allele with the insertion indicates a genetically normal horse (lp/lp), the presence of the insertion in one allele indicates that the horse is heterozygous for LP (lp/LP) and the presence of the insertion in both alleles indicates that the horse is homozygous for LP (LP/LP).

In one embodiment, the method disclosed herein can be used to identify the carriers of the recessive lp factor (LP/lp). As explained previously, a single autosomal dominant gene, Leopard Complex (LP), is responsible for inheritance of these coat patterns. Horses homozygous for leopard complex spotting (LP/LP) have fewer spots on the white patterned areas than heterozygotes (LP/lp) (see, for example, FIG. 1). Inheritance of the leopard complex spotting in horses can be in three forms: (1) LP/LP=few to no spots of pigment; (2) LP/lp=carrier (plentiful spots of pigment in white areas of coat); (3) lp/lp=true solid coat.

In one embodiment, the insertion is a 1378 base pair insertion. In another embodiment, the insertion is as shown in SEQ ID NO:1.

The phrase "detecting or selecting different coat patterns" refers to a method or process of determining if a horse has or does not have or will have or will not have a specific coat pattern, and includes determining the type of coat pattern.

The phrase "different coat patterns" as used herein refers to variations in coat color, coat spotting, and coat patterns.

The phrase "testing a sample from a horse to identify the presence of an insertion" as used herein includes, without limitation, obtaining a sample and sequencing a region of DNA or RNA surrounding the insertion site; obtaining a sample and testing the sample for hybridization with a probe that hybridizes to the insertion allele and a probe that hybridizes to the wild type TRPM1 allele and differentially detecting the presence of each probe, or obtaining a sample and amplifying from the sample a region surrounding and/or including the insertion site and analyzing the amplified region for the presence of the insertion for example detecting the size of the amplified region or by sequencing the region. The presence of the insertion could also be identified by Restriction Fragment Length Polymorphism, employing restriction sites containing in flanking genomic regions combined with unique restriction sites contained with the insert sequence. In one embodiment, three primers are used wherein a first primer and a second primer that flank the insertion site amplify the region of the wild type allele and the first primer and a third primer that is located within the insertion sequence amplify the region of the insertion allele, wherein the amplified regions are differentially detectable (see, for example, FIGS. 5 and 6). Primers and probes useful in the methods disclosed herein are further described below.

The phrase "differentially detectable" as used herein refers to the ability to differentiate between two products (amplified regions or hybridized regions or restriction fragments), for example, based on size or label.

In another embodiment, the methods for detecting or selecting coat patterns in a horse further comprise selecting a horse that has no allele with an insertion after position 108,297,929 of ECA1 and selecting a horse that has both alleles with an insertion after position 108,297,929 of ECA1, breeding the selected horses together to generate a horse with an LP/lp genotype. In yet another embodiment, the methods further comprise selecting two horses, each with both alleles with an insertion after position 108,297,929 of ECA1 and breeding the selected horses together to generate a horse with an LP/LP genotype. In yet a further embodiment, the methods further comprise selecting two horses, each with no alleles having an insertion after position 108,297,929 of ECA1 and breeding the selected horses together to generate a horse with an lp/lp genotype or selecting a horse with no allele having an insertion after position 108,297,929 of ECA1 and breeding the selected horse with a Thoroughbred, quarter horse, or other lp/lp horse to generate a horse with an lp/lp genotype. In yet another embodiment, the methods further comprise selecting two horses, each with one copy of an allele having an insertion after position 108,297,929 of ECA1 and breeding the horses to generate a horse with an LP/LP, LP/lp or lp/lp genotype. In yet another embodiment, the methods further comprise selecting two horses, the first with one allele having an insertion after position 108,297,929 of ECA1 and the second with both alleles having an insertion after position 108,297,929 of ECA1 and breeding the selected horses to generate a horse with an LP/LP or LP/lp genotype. In yet a further embodiment, the methods further comprise selecting two horses, the first with one allele having an insertion after position 108,297,929 of ECA1 and the second with no alleles having an insertion after position 108,297,929 of ECA1 and breeding the selected horses to generate a horse with an LP/lp or lp/lp genotype.

In yet another embodiment, the present disclosure provides a method for selecting horses for breeding to avoid CSNB in all foals comprising testing a sample obtained from a horse to detect the presence or absence of an insertion after position 108,297,929 on chromosome 1 in one or both alleles and breeding horses that are (i) heterozygous (one allele with the insertion) with genetically normal horses (no alleles with the insertion); or (ii) homozygous (both alleles with the insertion) with genetically normal horses (no alleles with the insertion), to generate foals for leopard complex spotting, while avoiding CSNB.

In one embodiment, the horse is an Appaloosa. In another embodiment, the horse is a Knabstrupper. In yet another embodiment, the horse is an American Miniature. In a further embodiment, the horse is a British Spotted Pony. In yet a further embodiment, the horse is a Pony of the Americas. In an even further embodiment, the horse is a Noriker.

It is contemplated that the methods described herein can be used in combination with other methods to select or detect horse coat patterns, including genotyping and/or phenotypic observations. As one example, the methods described herein can be used in combination with genetic testing of horse coat colour offered by many laboratories, including without limitation, by UC Davis Veterinary Genetics Lab; Genetic Technologies Corp., Victoria, Australia; Animal Genetics in Florida and the United Kingdom and/or VetGen in Ann Arbor, Mich. In another embodiment, the method can be used in combination with determining the LP genotype of the horse.

Agents to Detect the Insertion after Position 108,297,929 of ECA1

The determination of the presence of an insertion after position 108,297,929 of ECA1 as disclosed in the methods herein is optionally carried out by detecting binding of a nucleic acid sequence that specifically hybridizes to the allele having the insertion. Accordingly, in one embodiment, the present disclosure provides a probe that specifically hybridizes to the insertion after position 108,297,929 of ECA1. In particular, the probe specifically hybridizes to the 1378 base pair insertion sequence as shown in SEQ ID NO:1. In another embodiment, there is provided a composition comprising two probes, a probe that specifically hybridizes to the 1378 base pair insertion sequence as shown in SEQ ID NO:1 and a probe that specifically hybridizes to the TRPM1 wild type allele.

The term "a probe that specifically hybridizes to the insertion" as used herein refers to a nucleic acid or oligonucleotide that binds to a sequence from the allele with the insertion and not to a sequence from the wild type.

The term "a probe that specifically hybridizes to the wild type TRPM1 allele" as used herein refers to a nucleic acid or oligonucleotide that binds to a sequence from the wild type TRPM1 gene spanning the insertion site and that does not bind to the allele with the insertion sequence under stringent conditions.

The term "probe" as used herein refers to an isolated nucleic acid molecule or oligonucleotide having a nucleic acid sequence that will hybridize to a nucleic acid target sequence. In one example, the probe hybridizes to a TRPM1 DNA insertion sequence or a nucleic acid sequence complementary to the TRPM1 DNA insertion sequence. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length. A person skilled in the art could readily design various probes using the TRPM1 insertion and wild type sequences that would be useful in the methods disclosed herein.

The term "isolated nucleic acid" or "oligonucleotide" as used herein refers to a nucleic acid substantially free of cellular material or culture medium when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" or "oligonucleotide" is intended to include DNA and RNA and can be either double stranded or single stranded. The nucleic acid sequences contemplated by the present disclosure include isolated nucleotide sequences which hybridize to a RNA product or DNA of the present disclosure, nucleotide sequences which are complementary to the RNA product or DNA of the disclosure, nucleotide sequences which act as probes, or nucleotide sequences which are sets of specific primers.

The term "hybridize" refers to the sequence specific non-covalent binding interaction with a complementary nucleic acid. In one embodiment, the hybridization is under stringent hybridization conditions. In another embodiment, the hybridization is under moderately stringent conditions.

By "hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrid, is determined by the Tm, which in sodium containing buffers is a function of the sodium ion concentration and temperature (Tm=81.5° C.-16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm. For example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

In another embodiment, the determination of the presence of an insertion after position 108,297,929 of ECA1 as disclosed herein is optionally determined by analyzing the region comprising the insertion and the wild type sequence, for example, by sequencing the region surrounding position 108,297,929 of ECA1 or by amplifying a region surrounding position 108,297,929 of ECA1.

A person skilled in the art would readily be able to design primers wherein a first set of primers has a forward and reverse primer that prime amplification of a wild type sequence and a second set of primers that has a forward and a reverse primer that prime amplification of an allele having the insertion. Accordingly, primers can be used to amplify the wild type sequence and/or the insertion sequence and then the amplified regions can be differentially detected as described herein. In one embodiment, three primers are used, wherein a first primer and a second primer flank the insertion site and amplify the wild type sequence (although these primers would be expected to amplify the insertion allele, the product would be too large to be detectable under certain PCR conditions, for example, by choosing an appropriate extension time) and the first primer and a third primer that is located in the insertion sequence amplify the allele having the insertion.

In one embodiment, the present disclosure provides a primer that is used to amplify the allele with the insertion comprising SEQ ID NO:4. In another embodiment, the present disclosure provides a composition comprising three primers that are able to amplify an allele with the insertion sequence and a wild type allele to produce products that are differentially detectable. In a particular embodiment, the present disclosure provides a composition comprising three primers as shown in SEQ ID NOs:2-4.

The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand, is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

Kits

Another aspect of the present disclosure is a kit for screening, detecting or diagnosing congenital stationary night blindness (CSNB) or a predisposition to CSNB in a horse or detecting or screening horse coat patterns. In one embodiment, the kit comprises a probe that specifically hybridizes to the TRPM1 insertion allele as described herein. In another embodiment, the kit comprises a probe that specifically hybridizes to the TRPM1 insertion allele and a probe that specifically hybridizes to the wild-type allele, wherein the probes are differentially detectable, for example, distinctly labeled, such as, using different fluorophores, such as fluorophore 6-carboxyfluoroscein (FAM) and fluorophore 4,7,2'-trichloro-7'-phenyl-6-carboxyfluorescein (VIC).

In another embodiment, the present disclosure provides a kit for screening detecting or diagnosing congenital stationary night blindness or a predisposition to CSNB in a horse or detecting or screening horse coat patterns comprising specific primers that amplify a region of the allele with the TRPM1 insertion as disclosed herein. In one embodiment, the kit comprises three primers, wherein a first and a second primer that flank the insertion site (that is the insertion site located after position 108,297,929 of ECA1) amplify a region present in the wild type allele and the first primer and a third primer that is located in the insertion sequence amplify a region of allele with the TRPM1 insertion, wherein the amplified regions are distinguishable or differentially detectable for example by size or label.

The kits disclosed herein can also include instructions for use or ancillary agents. For example, the kits can include vessels for storing or transporting the probes and/or primers; a control; instruments for obtaining a sample; and/or buffers or stabilizers. The kits can also include sequencing reagents or detection agents for analysis.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

The present inventors have demonstrated the only definitive genetic test for LP and CSNB. Previous markers, while in tight linkage with the trait, cannot be guaranteed not to have false positive/negative results. Other methods of diagnosing CSNB, while more definitive, are extremely expensive and only available where a specialist in Veterinary Ophthalmology can be found.

The present inventors used whole transcriptome sequencing data followed by PCR and genomic DNA sequencing to identify and sequence an insertion of 1378 nucleotides after horse chromosome 1: 108,297,929 (see FIGS. 1 and 2). This insertion falls within an intron of TRPM1 (characterized as intron 1-2 of one isoform) which disrupts TRPM1 expression As shown in Table 1 below, this insertion is the causative mutation that disrupts expression of TRPM1 leading to the spotting and CSNB phenotypes. Allele specific primers were utilized for genotyping. Perfect association for the 1378 bp insertion with LP genotype in seven breeds (Appaloosas, Knabstruppers, Norikers, Australian Spotted Ponies, British Spotted Ponies, Pony of the Americas, and American Miniature Horses) ($x^2=1022.00$, $p<<0.0005$ N=511) and CSNB status in two breeds ($x^2=43$, $p<<0.0005$ N=43) was observed.

TABLE 1

| A. Spotting phenotype - all breeds combined | | | |
| --- | --- | --- | --- |
| Genotype for insertion in intron 1<br>N = 511, $X^2$ = 1022, P << 0.0005 | W/W | I/W | I/I |
| LP/LP (Spotting) | 0 | 0 | 125 |
| LP/lp (Spotting) | 0 | 248 | 0 |
| lp/lp (No Spotting) | 138 | 0 | 0 |
| B. CSNB (Appaloosas & American Miniature Horse) | | | |
| Genotype for insertion in intron 1<br>N = 43, $X^2$ = 43, P << 0.0005 | W/W | I/W | I/I |
| Affected | 0 | 0 | 17 |
| Unaffected | 14 | 12 | 0 |

I = insertion; W = wildtype (reference genome sequence)

The most frequently used method for genoptyping involved a system of three primers that produced different product sizes depending on presence or absence of the insertion. (DNA sequencing of genomic DNA was also used). The three primers used were as follows:

```
                                           (SEQ ID NO: 2)
5'-CCGACTTGGGTAGCAACTGA-3' (Forward primer F1 in

FIG. 5);

(SEQ ID NO: 3)
5'-CTCGGCAATCAGTGAATGAA-3' (Reverse primer in

Figure 5:
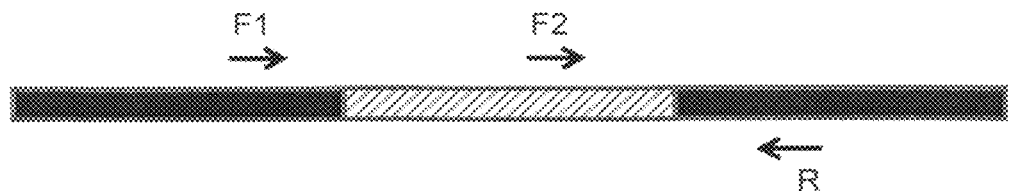
FIG. 5 is a schematic showing allele specific PCR design. The TRPM1 intron is represented in black and the insertion is represented by hatched fill. Primers are denoted by arrows with directions. F1 and R will amplify the wild type allele generating a 186 bp product whereas F2 and R will amplify the insertion, if present, generating a 225 bp product.

FIG. 5);
and (SEQ ID NO: 4)
5'-AAGGGCAGTTAAAAGCAGCA-3' (Forward primer F2 in

FIG. 5).
```

Figure 6:
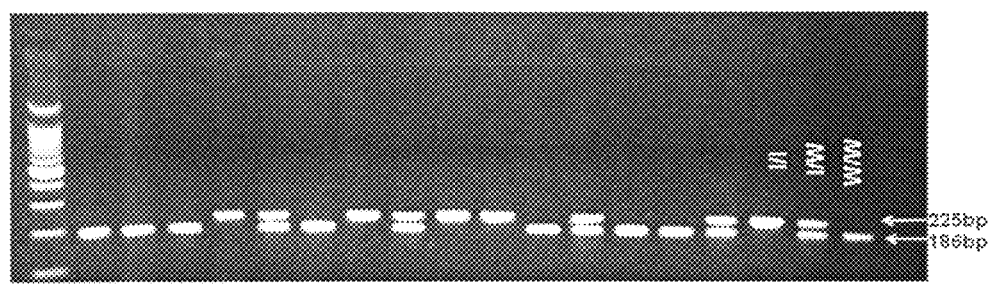
FIG. 6 shows a gel of the allele specific PCR products produced from the primers that differentially detect the wild type allele and the insertion allele. 3% agarose gel visualized with ethidium bromide, illuminated by ultraviolet light displaying the allele specific TRPM1 insertion PCR products. Lane 1 contained the size standard. Lanes 2-16 contained DNA from 15 different Appaloosa horses and lanes 17-20 contained DNA from 3 positive controls and one negative control. The size of the two products is 225 base pairs and 186 base pairs.

A PCR product of 225 bp indicates the LP allele while a 186 bp product is indicates the wild type allele (FIG. 6).

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Audo I, Kohl S, Leroy B P et al. TRPM1 is mutated in patients with autosomal recessive complete congenital stationary night blindness. American Journal of Human Genetics 2009; 85:720-729.

Bellone, R., T. Lear, D. L. Adelson and E. Bailey, 2006a Comparative mapping of oculocutaneous albinism type II (OCA2), transient receptor potential cation channel, subfamilyMmember 1 (TRPM1) and two equine microsatellites, ASB08 and 1CA43, among four equid species by fluorescence in situ hybridization. Cytogenet. Genome Res. 114: 93A.

Bellone R R, Brooks S A, Sandmeyer L, et al. Differential gene expression of TRPM1, the potential cause of congenital stationary night blindness and coat spotting patterns (LP) in the Appaloosa horse (*Equus caballus*). Genetics. 2008; 179:1861-1870.

Bellone, R., S. Lawson, N. Hunter, S. Archer and E. Bailey, 2006b Analysis of a SNP in exon 7 of equine OCA2 and its exclusion as a cause for appaloosa spotting. Anim. Genet. 37: 525.

Bellone, R., G. Forsyth, T. Leeb, S. Archer, S. Sigurdsson, F. Imsland, E. Mauceli, M. Engensteiner, E. Bailey, L. Sandmeyer, B. Grahn, K. Lindblad-Toh, and C. M. Wade, 2010 Fine-mapping and mutation analysis of TRPM1: a candidate gene for leopard complex (LP) spotting and congenital stationary night blindness in horses. Briefings in Functional Genomics. Vol. 9, no. 3, 193-207.

Bellone, R., S. Archer, C. M. Wade, C. Cuka-Lawson, B. Haase, T. Leeb, G. Forsyth, L. Sandmeyer, and B. Grahn, 2010 Association analysis of candidate SNPs in TRPM1 with leopard complex spotting (LP) and congenital stationary night blindness (CSNB) in horses. Animal Genet. 41: Suppl. S2, 207.

Berger, S. A., 2006 Signaling pathways influencing SLF and c-kit mediated survival and proliferation. Immunol. Res. 35: 1-12.

Brooks, S. A., and E. Bailey, 2005 Exon skipping in the KIT gene causes a Sabino spotting pattern in horses. Mamm. Genome 11: 893-899.

Brooks, S., T. L. Lear, D. Adelson and E. Bailey, 2007 A chromosome inversion near the KIT gene and the Tobiano spotting pattern in horses. Cytogenet. Genome Res. 119: 225-230.

Brunberg, E., L. Andersson, G. Cothran, K. Sandberg, S. Mikko et al., 2006 A missense mutation in PMEL17 is associated with the silver coat color in the horse. BMC Genet. 7: 46.

Clapham, D. E., L. W. Runnels and C. Strubing, 2001 The TRP ion channel family. Nat. Rev. Neurosci. 2: 387-396.

Deeds, J., F. Cronin and L. M. Duncan, 2000 Patterns of melastatin mRNA expression in melanocytic tumors. Hum. Pathol. 31: 1346-1356.

Duncan, L. M., J. Deeds, J. Hunter, J. Shao, L. M. Homgren et al., 1998 Down-regulation of the novel gene melanstatin correlates with potential for melanomametastasis. Cancer Res. 58: 1515-1520.

Duncan, L. M., J. Deeds, F. E. Cronin, M. Donovan, A. J. Sober et al., 2001 Melastatin expression and prognosis in cutaneous malignant melanoma. J. Clin. Oncol. 19: 568-576.

Erickson, C. A., 1993 From the crest to the periphery: control of pigment cell migration and lineage segregation. Pigment Cell Res. 6: 336-347.

Fang, D., and V. Setaluri, 2000 Expression and up-regulation of alternatively spliced transcripts of melastatin, a melanoma metastasis-related gene, in human melanoma cells. Biochem. Biophys. Res. Commun. 279: 53-61.

Gommerman, J. L., and S. A. Berger, 1998 Protection from apoptosis by steel factor but not interleukin-3 is reversed through blockade of calcium influx. Blood 91: 1891-1900.

Haase, B., S. A. Brooks, A. Schlumbaum, P. Azor, E. Bailey et al., 2007. Allelic heterogeneity at the equine KIT locus in dominant white (W) horses. PLoS Genet. 3: e195.

Hunter, J. J., J. Shao, J. S. Smutko, B. J. Dussault, D. L. Nagle et al., 1998 Chromosomal localization and genomic characterization of the mouse melastatin gene (Mlsn1). Genomics 54: 116-123.

Kim, C., 2004 Transient receptor ion channels and animal sensation: lessons from *Drosophila* functional research. J. Biochem. Mol. Biol. 37: 114-121.

Lapp, R. A., and G. Carr, 1998 Applied appaloosa color genetics. Appaloosa J. 52: 113-115.

Li Z, Sergouniotis P I, Michaelides M et al. Recessive mutations of the gene TRPM1 abrogate ON bipolar cell function and cause complete congenital stationary night blindness in humans. American Journal of Human Genetics 2009; 85: 711-719.

Mariat, D., S. Taourit and G. Guerin, 2003 A mutation in the MATP gene causes the cream coat colour in the horse. Genet. Sel. Evol. 35: 119-133.

Marklund, L., M. J. Moller, K. Sandberg and L. Andersson, 1996 A missensemutation in the gene for melanocyte-stimulating hormone receptor (MC1R) is associated with the chestnut coat color in horses. Mamm. Genome 7: 895-899.

Metallinos, D. L., A. T. Bowling and J. Rine, 1998 A missense mutation in the endothelin-B receptor gene is associated with Lethal White Foal Syndrome: an equine version of Hirschsprung disease. Mamm. Genome 9: 426-431.

Miller, R. W., 1965 Appaloosa coat color inheritance. Ph.D. Thesis, Animal Science Department, Montana State University, Bozeman, Mont.

Morgans C W, Zhang J, Jeffrey B G et al. TRPM1 is required for the depolarizing light response in retinal ON-bipolar cells. Proceedings of the National Academy of Science USA 2009; 106: 19174-19178.

Nakamura M, Sanuki R, Yasuma T R et al. TRPM1 mutations are associated with the complete form of congenital stationary night blindness. Molecular Vision 2010; 16: 425-437.

Nakanishi, S., Y. Nakajima, M. Masu, Y. Ueda, K. Nakahara et al., 1998 Glutamate receptors: brain function and signal transduction. Brain Res. Rev. 26: 230-235.

Nilius, B., 2007 TRP channels in disease. Biochim. Biophys. Acta 1772: 805-812.

Nomura, M., H. Iwakabe, Y. Tagawa, T. Miyoshi, Y. Yamashita et al., 1994 Developmentally regulated postsynaptic localization of a metabotropic glutamate receptor in rat rod biopolar cells. Cell 77: 361-369.

Rebhun, W. C., E. R. Loew, R. C. Riis and L. J. Laratta, 1984 Clinical manifestations of night blindness in the Appaloosa horse. Comp. Contin. Edu. Pract. Vet. 6: S103-S106.

Rieder, S., S. Taourit, D. Mariat, B. Langlois and G. Guei'rin, 2001 Mutations in the agouti (ASIP), the extension (MC1R), and the brown (TYRP1) loci and their association to coat color phenotypes in horses (*Equus caballus*). Mamm. Genome 12: 450-455.

Sandmeyer, L., C. B. Breaux, S. Archer and B. H. Grahn, 2007 Clinical and electroretinographic characteristics of congenital stationary night blindness in the Appaloosa and the association with the leopard complex. Vet. Ophthalmol. 10: 368-375.

Sandmeyer, L., Bellone, R., Archer, S., Bauer, B., Nelson, J., Forsyth, G. and B. Grahn. 2011 Congenital Stationary Night Blindness is Associated with the Leopard Complex in the Miniature Horse. Vet. Opthalmol. 1-5.

Schubert, G., and H. Bornshein, 1952 Beitrag zur A lyse des menschlichen Electroretinogram. Ophthalmolgica 123: 396-413.

Shen Y, Heimel J A, Kamermans M, Peachey N S, Gregg R G, Nawy S. A transient receptor potential-like channel mediates synaptic transmission in rod bipolar cells. J. Neurosci. 2009; 29:6088-6093.

Sponenberg, D. P., and B. V. Beaver, 1983 Horse Color. Texas A&M Press, College Station, Tx.

Sponenberg, D. P., G. Carr, E. Simak and K. Schwink, 1990 The inheritance of the leopard complex of spotting patterns in horses. J. Hered. 81: 323-331.

Sponenberg, D. P., Archer, S., & Bellone, R. (2009) Patters of White with Symmetric White Patches: the Leopard Complex. In: Sponenberg D P. Equine Color Genetics. 3rd Edition. Ames, Iowa: Iowa State University Press, pp 110-121.

Steingrimsson, E., N. G. Copeland and N. A. Jenkins, 2006 Mouse coat color mutations: from fancy mice to functional genomics. Dev. Dyn. 235: 2401-2411.

Stryer, L., 1991 Visual excitation and recovery. J. Biol. Chem. 266: 10711-10714.

Terry, R. B., S. Archer, S. Brooks, D. Bernoco and E. Bailey, 2004 Assignment of the appaloosa coat colour gene (LP) to equine chromosome 1. Anim. Genet. 35: 134-137.

van Genderen M M, Bijveld M M, Claassen Y B et al. Mutations in TRPM1 are a common cause of complete congenital stationary night blindness. American Journal of Human Genetics 2009; 85:730-736.

Witzel, D. A., J. R. Joyce and E. L. Smith, 1977a Electroretinography of congenital night blindness in an Appaloosa filly. J. Eq. Med. Surg. 1: 226-229.

Witzel D A, Riis R C, Rebhun W C et al. Night blindness in the Appaloosa: sibling occurrence. Journal of Equine Medicine and Surgery 1977; 1: 383-386.

Witzel, D. A., E. L. Smith, R. D. Wilson and G. D. Aguirre, 1978 Congenital stationary night blindness: an animal model. Invest. Ophthalmol. Vis. Sci. 1978(117): 788-793.

Xu, X. Z., F. Moebius, D. L. Gill and C. Montell, 2001 Regulation of melastatin, a TRP-related protein, through interaction with a cytoplasmic isoform. Proc. Natl. Acad. Sci. USA 98: 10692-10697.

Zhiqi, S., M. H. Soltani, K. M. Bhat, N. Sangha, D. Fang et al., 2004 Human melastatin 1 (TRPM1) is regulated by MITF and produces multiple polypeptide isoforms in melanocytes and melanoma. Melanoma Res. 14: 509-516.

The invention claimed is:

1. A method of screening for, diagnosing or detecting congenital stationary night blindness (CSNB) or detecting or selecting different coat patterns in a horse comprising:
   (a) amplifying a sample from a the horse with three primers to identify the presence of an insertion of SEQ ID NO: 1 in the TRPM1 gene after position 108,297,929 of horse chromosome 1 (ECA1), wherein the primers are SEQ ID NOs: 2-4 and
   (b) identifying the horse as a true solid coat coloured horse and genetically normal for CSNB (lp/lp) if the allele with the insertion is absent,
   identifying the horse as a spotted horse heterozygous for LP and a carrier for CSNB (LP/lp) if the insertion is present in one allele and
   identifying the horse as a spotted horse homozygous for LP and that the horse is affected with or predisposed to CSNB (LP/LP) if the insertion is on both alleles.

2. The method of claim 1, wherein the horse is an Appaloosa horse, American Miniature Horse, British Spotted Pony, Pony of the Americas, Noriker or a Knabstrupper horse.

3. The method of claim 1, further comprising (c) managing the CSNB if the horse is homozygous for the insertion.

4. A method of breeding a spotted horse heterozygous for LP and a carrier for CSNB having the LP/lp genotype comprising:
   (a) testing a sample from a horse to identify the presence of an insertion of SEQ ID NO: 1 in the TRPM1 gene after position 108,297,929 of horse chromosome 1 (ECA1),
   (b) identifying the horse as genetically normal for congenital stationary night blindness (CSNB) or as a true solid coat coloured horse (lp/lp) if the allele with the insertion is absent,
   identifying the horse as a spotted horse heterozygous for LP and a carrier for CSNB (LP/lp) if the insertion is present on one allele and
   identifying the horse as a spotted horse homozygous for LP and that the horse is affected with or predisposed to CSNB (LP/LP) if the insertion is on both alleles,
   (c) selecting a horse that has no allele with an insertion (lp/lp) and a horse that has both alleles with an insertion (LP/LP), and
   (d) breeding the horses together to generate a horse with an LP/lp genotype.

5. A method of breeding a spotted horse homozygous for LP and affected with or predisposed to CSNB having the LP/LP genotype comprising:
   (a) testing a sample from a horse to identify the presence of an insertion of SEQ ID NO: 1 in the TRPM1 gene after position 108,297,929 of horse chromosome 1 (ECA1),
   (b) identifying the horse as genetically normal for congenital stationary night blindness (CSNB) or as a true solid coat coloured horse (lp/lp) if the allele with the insertion is absent,
   identifying the horse as a spotted horse heterozygous for LP and a carrier for CSNB (LP/lp) if the insertion is present on one allele and
   identifying the horse as a spotted horse homozygous for LP and that the horse is affected with or predisposed to CSNB (LP/LP) if the insertion is on both alleles,
   (c) selecting two horses, each with both alleles with the insertion (LP/LP), and
   (d) breeding the horses together to generate a horse with an LP/LP genotype.

6. A method of breeding a horse that is genetically normal for congenital stationary night blindness (CSNB) or that is a true solid coat coloured horse having the lp/lp genotype comprising:
   (a) testing a sample from a horse to identify the presence of an insertion of SEQ ID NO: 1 in the TRPM1 gene after position 108,297,929 of horse chromosome 1 (ECA1),
   (b) identifying the horse as genetically normal for CSNB or as a true solid coat coloured horse (lp/lp) if the allele with the insertion is absent,
   identifying the horse as a spotted horse heterozygous for LP and a carrier for CSNB (LP/lp) if the insertion is present on one allele and
   identifying the horse as a spotted horse homozygous for LP and that the horse is affected with or predisposed to CSNB (LP/LP) if the insertion is on both alleles,
   (c) selecting two horses, each with no alleles with the insertion (lp/lp), and
   (d) breeding the horses together to generate a horse with an lp/lp genotype.

7. A method of breeding a horse having an LP/LP, LP/lp, or lp/lp genotype comprising:
   (a) testing a sample from a horse to identify the presence of an insertion of SEQ ID NO: 1 in the TRPM1 gene after position 108,297,929 of horse chromosome 1 (ECA1),
   (b) identifying the horse as genetically normal for congenital stationary night blindness (CSNB) or as a true solid coat coloured horse (lp/lp) if the allele with the insertion is absent, identifying the horse as a spotted horse heterozygous for LP and a carrier for CSNB (LP/lp) if the insertion is present on one allele and identifying the horse as a spotted horse homozygous for LP and that the horse is affected with or predisposed to CSNB (LP/LP) if the insertion is on both alleles, (c) selecting two horses, each with one allele with an insertion (LP/lp), and (d) breeding the horses together to generate a horse with an LP/LP, LP/lp or lp/lp genotype.

8. A method of breeding a horse having the LP/LP or LP/lp genotype comprising:

(a) testing a sample from a horse to identify the presence of an insertion of SEQ ID NO: 1 in the TRPM1 gene after position 108,297,929 of horse chromosome 1 (ECA1), (b) identifying the horse as genetically normal for congenital stationary night blindness (CSNB) or as a true solid coat coloured horse (lp/lp) if the allele with the insertion is absent, identifying the horse as a spotted horse heterozygous for LP and a carrier for CSNB (LP/lp) if the insertion is present on one allele and identifying the horse as a spotted horse homozygous for LP and that the horse is affected with or predisposed to CSNB (LP/LP) if the insertion is on both alleles, (c) selecting a horse with one allele with an insertion (LP/lp) and a horse with both alleles with an insertion (LP/LP), and (d) breeding the horses together to generate a horse with an LP/LP or LP/lp genotype.

9. A method of breeding a horse having the LP/lp or lp/lp genotype comprising:

(a) testing a sample from a horse to identify the presence of an insertion of SEQ ID NO: 1 in the TRPM1 gene after position 108,297,929 of horse chromosome 1 (ECA1), (b) identifying the horse as genetically normal for congenital stationary night blindness (CSNB) or as a true solid coat coloured horse (lp/lp) if the allele with the insertion is absent, identifying the horse as a spotted horse heterozygous for LP and a carrier for CSNB (LP/lp) if the insertion is present on one allele and identifying the horse as a spotted horse homozygous for LP and that the horse is affected with or predisposed to CSNB (LP/LP) if the insertion is on both alleles, (c) selecting a horse with one allele having an insertion (LP/lp) and a horse with no alleles with an insertion (lp/lp), and (d) breeding the horses together to generate a horse with an LP/lp or lp/lp genotype.

* * * * *